United States Patent [19]

Cumming

[11] Patent Number: 5,047,051
[45] Date of Patent: Sep. 10, 1991

[54] INTRAOCULAR LENS WITH HAPTIC ANCHOR PLATE

[76] Inventor: J. Stuart Cumming, 1211 W. La Palma, Suite 201, Anaheim, Calif. 92801

[21] Appl. No.: 515,189
[22] Filed: Apr. 27, 1990
[51] Int. Cl.⁵ .............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,242,762 | 1/1981 | Tennant | 623/6 |
| 4,244,060 | 1/1981 | Hoffer | 623/6 |
| 4,673,406 | 6/1987 | Schegel | 623/6 |
| 4,726,367 | 2/1988 | Shoemaker | 623/6 X |
| 4,846,832 | 7/1989 | Wichterle | 623/6 |

FOREIGN PATENT DOCUMENTS

| | | | |
|---|---|---|---|
| 0175972 | 4/1986 | European Pat. Off. | 623/6 |
| 2124500A | 2/1984 | United Kingdom | 623/6 |

Primary Examiner—Ronald Frinks

[57] ABSTRACT

An intraocular lens having an optic region and an anchor plate attached to the optic region and extending radially outwardly therefrom at diametrically opposite ends of the optic regions, and a pair of resilient haptic loop members attached to the anchor plate and displaced thereby from the optic region.

16 Claims, 2 Drawing Sheets

INTRAOCULAR LENS WITH HAPTIC ANCHOR PLATE

BACKGROUND OF THE INVENTION

Surgical removal of the opaque lens from the eyes of cataract patients is one of the most common surgical procedures. In the past, contact lenses or spectacles were usually prescribed for the patient to provide at least limited vision following the operation. However, there were many drawbacks to the use of contact lenses and spectacles for such purposes. The present-day practice involves the implantation of an artificial intraocular lens to replace the removed opaque human lens as a preferred procedure to restore the patient's sight. The first intraocular lens was inserted in 1949 by Harold Ridley in England.

The eye is divided by the iris into an anterior chamber in front of the iris and a posterior chamber behind the iris and in front of the human lens. The intraocular lens can be placed either in the anterior chamber or the posterior chamber. Placement in the posterior chamber is preferred because the lens can simply be positioned by the use of centering haptic loops or the like extending from the lens body. Such an intraocular lens is described, for example, in U.S. Pat. No. 4,634,441 Clayman et al.

Until recent years intraocular lenses have been constructed of hard material, such as glass or plastic. Typically the lens body of the prior art intraocular lens is formed of polymethylmethacrylate (PMMA) and the haptics have been formed of polypropylene (PROLENE). However, PMMA is a hard material and the lenses made from this material usually have a diameter of between 6 and 7 mm. This requires an incision of 7–8 mm in order to insert the lens into the eye. Accordingly, proposals have been made in the past to form the intraocular lens of a soft flexible material such as silicone or hydrophilic polymer which can be folded.

Moreover, those skilled in the art of cataract extraction have long recognized the need to develop a foldable or compressible lens that will pass through a small incision of 4 mm or less. The advantages of a small include reduced complications, more rapid visual and physical rehabilitation, and reduced costs. A method for implanting a deformable intraocular lens into the eye is described, for example, in U.S. Pat. No. 4,573,998. Deformable intraocular lenses made primarily of HEMA (hydroxyethylmethylmethacrylate) and silicone have been developed that will pass through incisions of 4 mm or less.

However, difficulties have been encountered in the design of soft deformable intraocular lenses, and such problems have consisted mainly in staking the haptic onto the soft optical zone of the intraocular lens. The PROLENE haptic, when anchored onto the optical zone necessitates thickening the edge of the optical zone in order to accommodate the staked end of haptic. This reduces the useful optical zone of the lens down to 4.5 mm when it should be 6 mm. In addition, it is proven difficult to attach the haptic to the optical zone of the soft deformable intraocular lens, since it is essential that the haptic has a constant angular relationship with the optical zone. For that reason, the rejection rate in manufacturing of present-day soft intraocular lenses is high and, therefore, the cost of acceptable soft deformable intraocular lenses is also high.

It is well known that some of the prior art intraocular lenses are misplaced during insertion so that one or both of the haptic loops are inadvertently inserted into the sulcus. The sulcus is longer than the capsular bag into which the lens was intended to be placed, and thus the prior art intraocular lens must have haptic loops long enough to fix the intraocular lens into the sulcus should it be misplaced. Otherwise, the misplaced lens could be decented within the eye.

It is known to attach the haptic loops to the optical region of an intraocular lens. Such a construction is disclosed, for example, in U.S. Pat. Nos. 4,834,751 and 4,790,846. However, the present invention provides a soft deformable intraocular lens having a rigid haptic anchor plate attached to the opposite ends of the optical region of the lens.

The haptic anchor plate is designed so that there is no loss of the optical zone. The anchor plate provides a base into which relatively short looped haptics formed, for example, or PROLENE or polyamide, can be staked, allowing for a large staking area of adequate thickness, without affecting the dimensions of the optical zone itself. Moreover, the haptic anchor plate makes decentration of the intraocular lens impossible when the lens is placed in the capsular bag, because the anchor plates are rigid enough to resist deformation when capsule fibrosis occurs and because the length of the lens is at least as long as the diameter of the capsular bag.

In the construction of the intraocular lens of the invention, with a flexible material the provision of the semi-rigid haptic anchor plate and the relatively short haptic arcuate resilient members or loops attached to the anchor plate provide a construction which enables the intraocular lens to be compressed for insertion through a small incision without damage to the haptic loops. This is an important feature, because it has been found that attempts to compress soft intraocular lenses having relatively long haptic loops attached to the optical region is difficult and frequently causes damage to the lens. In addition, the possibility of decentration after insertion of the lens is reduced because the semi-rigid haptic anchor plate resists folding or compression by the fibrosis of the human capsular bag, unlike the long PROLENE haptics of conventional intraocular lenses.

In the embodiment of the invention to be described, grooves are formed at the end edges of the rigid haptic anchor plate which receive the haptic loops when the intraocular lens is correctly placed in the capsular bag. During such placement, the ends of the haptic anchor plate containing the haptic loops engage the margins of the capsular bag holding the intraocular lens correctly centered and in place. However, if the intraocular lens is misplaced into the sulcus, the haptic loops will spring outwardly and extend beyond the ends of the anchor plate and press against the sulcus and stabilize the intraocular lens within the eye of the recipient. Accordingly, complications are prevented should the intraocular lens be misplaced within the eye, which studies have revealed to happen approximately 50% of the time.

The intraocular lens of the invention can be folded and compressed through a 3–4 mm phacoemulsification incision, or it can be used in the routine planned extracapsular cataract extraction with a large 15 mm incision. Decentration of the intraocular lens of the invention is virtually eliminated when the lens is placed in the capsular bag, as mentioned above, due to the haptic anchor plate, this plate being used not only to provide a base for affixing the haptic loops to the lens, but also for lens fixation in the capsular bag, with the flexible haptic loops being used when the lens is intentionally or accidentally placed in the sulcus.

In the lens of the invention, the PROLENE haptic loops are staked into two thickened edges of the haptic anchor plate. As mentioned above, this allows for a large staking area without any reduction in the optical zone of the intraocular lens. This is a distinct improvement over conventional intraocular lenses which have the haptic loops staked directly into the optic zone, thus reducing the optic zone of the lens between the stakes. The staking is done on the edge of the haptic anchor plate to facilitate folding of the intraocular lens when it is used in small incision surgery.

As will be described, grooves at the end of the haptic anchor plate allows the haptic loops to be compressed into the haptic anchor plate during the compression of the intraocular lens for insertion through a small incision. This protects the haptic loops from damage during compression and insertion of the intraocular lens through a small incision.

Also, the overall length of the lens and anchor plate is perferrably made equal to the transverse dimension of the capsular bag, and the lens and anchor plate are made sufficiently rigid, so that the posterior capsule is pulled tight against the posterior surface of the lens to prevent opacification of the posterior capsule.

The prior art resilient loop haptic lenses have a tendency to decenter because the haptic loops have very little resistance to forces of fibrosis of the capsular bag during healing. The intraocular lens of the present invention with the relatively rigid integral haptic anchor plate, which has a length corresponding to the length of the lens bag into which it is to be fitted, effectively eliminates any tendency for the intraocular lens to decenter.

The haptic anchor plate is preferably made of silicone, and has sufficient rigidity to resist the forces of fibrosis. Accordingly, as mentioned above, there is no tendency for the intraocular lens of the present invention to decenter. The haptic loops preferably extend to 13 mm so that if the intraocular lens is inadvertently placed in the sulcus, it will remain centered, as explained above. The intraocular lens of the invention also resists deformation when it is "shrink wrapped" by the capsular bag into which it has been inserted. This latter action causes the posterior elastic capsule to be pulled tightly against the posterior surface of the intraocular lens and greatly reduces opacification of the posterior capsule.

DETAILED DESCRIPTION OF THE ILLUSTRATED EMBODIMENT

Figure 2:
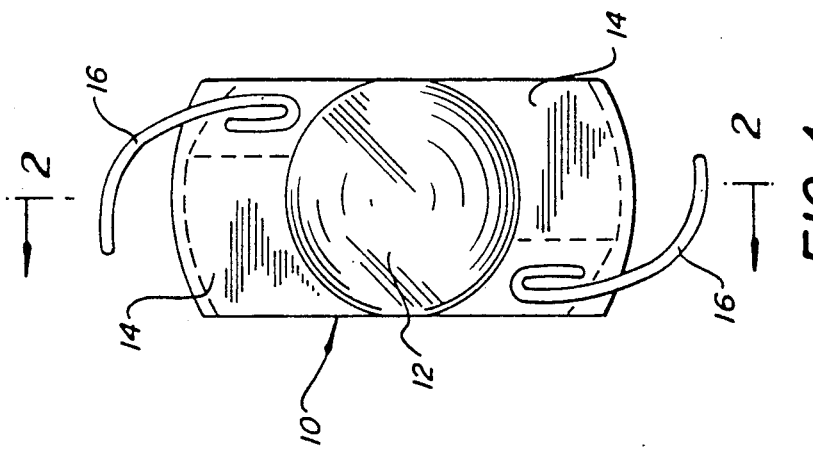
FIG. 2 is a sectional view taken substantially along the line 2—2 of FIG. 1.
Figure 1:
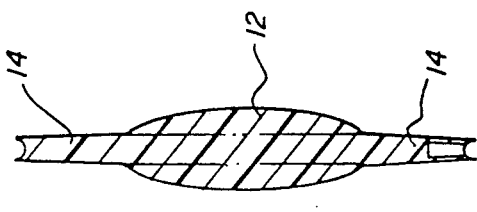
FIG. 1 is a top plan view of an intraocular lens and haptic anchor plate constructed in accordance with one embodiment of the invention.

The intraocular lens of FIGS. 1 and 2 is designated generally as 10 which may be a single or multifocal optical system. The lens includes a central disc-shaped optic portion 12 and an essentially rectangular haptic anchor plate 14 attached to the optic portion.

As best shown in FIG. 1, the haptic anchor plate 14 has a width essentially equal to the diameter of the optic portion 12, and a length greater than the diameter of the optic portion. The haptic anchor plate 14 extends radially outwardly from the optic portion 12 at diametrically opposite ends of the optic portion, as shown in FIG. 1. The haptic anchor plate is sufficiently rigid to prevent deformation during fibrosis, as explained above. As also explained, the length of the haptic anchor plate corresponds to that of the capsular bag in which the lens is intended to be placed. These two factors prevent decentration of the intraocular lens when placed in the capsular bag.

In accordance with the invention, the intraocular lens 10 of FIG. 1 includes a pair of haptic arcuate resilient members on loops 16 which are staked to the extended end portions of the anchor plate 14. The haptic loops 16 are shorter than those usually employed in prior art intraocular lenses, this being possible because of the length of the haptic anchor plate 14. The haptic loops are staked to a thickened part of the haptic anchor plate 14 to one side, as shown in FIG. 1, to facilitate folding of the intraocular lens.

As shown in FIGS. 1 and 2, grooves are formed in the end edges of the haptic anchor plate 14 which serve to receive the haptic loops 16 when the haptic loops are compressed down adjacent to the end edges into the grooves. The haptic loops 16 are completely compressed into the grooves when the intraocular lens is placed in the capsular bag. For such a placement, the lens is held in position by the haptic anchor plate 14, and rigidity of the haptic anchor plate maintains the lens centered in the capsular bag.

However, should the lens be placed in the sulcus, the loops 16 spring out the grooves, and engage the sides of the sulcus so that the lens is firmly held in the sulcus, should that placement occur.

Accordingly, the construction of the intraocular lens of the invention, as shown in FIGS. 1 and 2, assures that there will be a predetermined orientation of the intraocular lens in the eye, and also assure that the intraocular lens will not be subject to angular or linear movement within the eye, regardless of whether the lens is properly placed in the capsular bag, or it is placed in the sulcus. In addition, the short haptic loops are staked to the haptic anchor plate 14 at positions such that the intraocular lens 10 may be compressed for insertion through a small incision without damage to the haptic members. Also, and as described above, decentration of the intraocular lens within the eye is minimized because the semi-rigid haptic anchor plate 14 resists folding and compression, unlike the relatively long haptic loops of the conventional intraocular lenses.

The optic portion 12 of the intraocular lens of the invention may be formed of a soft foldable transparent plastic such as hydroxyethylmethylmethacrylate. The haptic anchor plate 14 may be formed of any appropriate relatively rigid material. The haptic loops 16 may be formed, for example, of polypropylene (PROLENE), or other appropriate resilient material.

Figure 3:
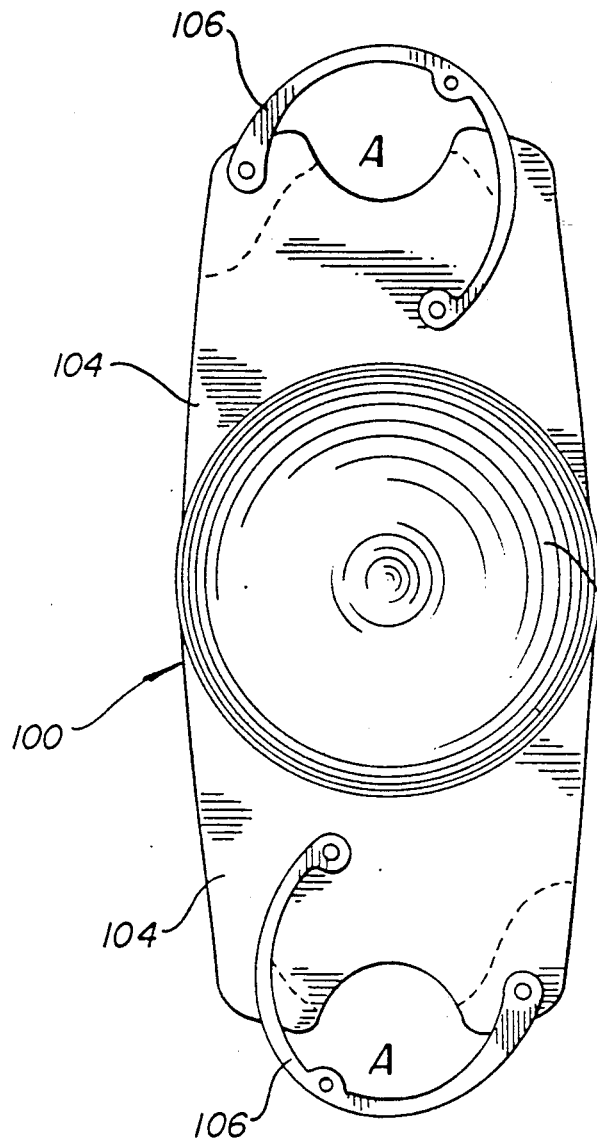
FIGS. 3–5 top plan views of further embodiments.

The intraocular lens of FIG. 3 is designated 100. It includes a central disc-shaped optic portion 102 and an anchor plate 104. A pair of haptic loops 106 are staked to the extended end portions of the anchor plate 104. One or both ends of each haptic loop 106 may be staked to the anchor plate 104. The haptic loops 106 and the haptic anchor plate 104 are configured, as shown, so that spaces "A" are left between the loops and the anchor plate.

The spaces permit the anterior and posterior capsules to fuse together by fibrosis after the intraocular lens has been inserted into the bag and the loops have been compressed. This fusion firmly fixes the intraocular lens in the bag and prevents its dislocation should it become necessary to open the posterior capsule with a Y.A.G. Laser at a later date.

Figure 4:
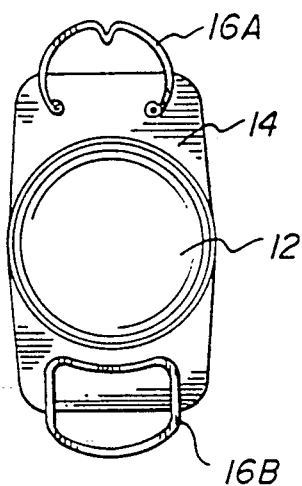

FIG. 4 shows an embodiment in which both ends of the haptic loops 16A, and 16B are anchored to the anchor plate 14. Loop 16A is notched for insertion purposes.

Figure 5:
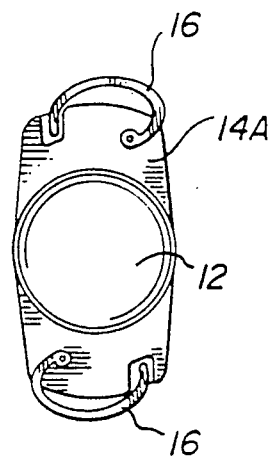

FIG. 5 shows an embodiment in which each end of the haptic anchor plate 14A is notched to receive the end of the corresponding haptic 16. The haptics are pushed all the way into the notches when the intraocular lens is placed in the bag, and partially into the notches when the lens is placed in the Sulcus.

The invention provides, therefore, an improved intraocular lens/anchor plate combination which enables haptic members to be attached to the lens without any reduction in the optic region, and which exhibits other distinct advantages set forth above.

It will be appreciated that while particular embodiments of the invention have been shown and described, modifications may be made. It is intended in the claims to cover all modifications which come within the true spirit and scope of the invention.

I claim:

1. An intraocular lens comprising: a disc-shaped central optic member; a haptic anchor plate attached to said optic member in essentially co-planar relationship therewith, said haptic anchor plate having a width essentially equal to the diameter of said optic member and a length greater than the diameter of said optic member so that said anchor plate extends radially outwardly from said optic member at opposite ends thereof, the length of said haptic anchor plate corresponding to the transverse dimension of the capsule bag in the eye of the recipient into which the lens is intended to be inserted to hold the lens in said capsular bag, and said haptic anchor plate being sufficiently rigid to resist deformation when fibrosis of the capsular bag occurs; and a pair of arcuate resilient haptic members attached to said anchor plate at opposite ends thereof to be compressed down adjacent to the end edges of the haptic anchor plate when the lens is positioned in the capsular bag of the eye of the recipient, and to spring outwardly from the ends of the haptic anchor plate when the lens is positioned in the sulcus of the eye of the recipient for positioning said intraocular lens in the sulcus.

2. The intraocular lens defined in claim 1, in which said haptic loop members are formed of polypropylene.

3. The intraocular lens defined in claim 1, in which said optic member is formed of hydroxyethylmethylmethacrylate.

4. The intraocular lens defined in claim 1, in which said optic member and said anchor plate are formed of a hard rigid plastic material.

5. The intraocular lens defined in claim 1, in which said haptic members are formed of polyamide.

6. The intraocular lens defined in claim 1, in which said optic member and said anchor plate are formed of silicone.

7. The intraocular lens defined in claim 1, in which the edges of said haptic anchor plate at the respective ends thereof have grooves formed therein to receive the arcuate haptic member when the haptic members are compressed down into the grooves by the capsular bag.

8. An intraocular lens comprising: an optic portion; a haptic anchor plate extending radially outwardly from said optic portion at diametrically opposite ends thereof and attached thereto, said haptic anchor plate having a length corresponding to the transverse dimension of the capsular bag of the eye of the recipient into which the lens is intended to be inserted to hold the lens in said capsular bag, and said haptic plate being sufficiently rigid to resist deformation when fibrosis of the capsular bag occurs; and a pair arcuate resilient haptic members attached to said anchor plate at opposite ends thereof to be compressed down adjacent to the end edges of the haptic anchor plate when the lens is positioned in the capsular bag of the eye of the recipient, and to spring outwardly from the ends of the haptic anchor plate when the lens is positioned in the sulcus of the eye of the recipient for positioning said intraocular lens in said sulcus.

9. The intraocular lens defined in claim 8, in which said optic portion is formed of foldable plastic material.

10. The intraocular lens defined in claim 8, in which said haptic members are formed of a resilient plastic material.

11. The intraocular lens defined in claim 8, which is configured so that a space is provided between each of the haptic members and the anchor plate when the lens is inserted into the capsular bag to permit the anterior and posterior capsules of the eye to fuse together through said space by fibrosis and firmly fix the lens in the eye.

12. The intraocular lens defined in 8, in which each of said haptic members is attached at both ends to said anchor plate.

13. The intraocular lens defined in claim 8, in which each of said haptic members is staked at one end only to said anchor plate.

14. The intraocular lens defined in claim 13, in which each end of said anchor plate is notched to receive the free end of the correspondence haptic member.

15. The intraocular lens is defined in claim 8, in which the edges of the haptic plate at the respective ends thereof have grooves formed therein to receive the arcuate haptic members when the haptic members are compressed down into grooves by the capsular bag.

16. The intraocular lens defined in claim 1, in which said optic member and said anchor plate are formed of a flexible optical material such as Hydroxyethylmethylmethacrylate.

* * * * *